US010765660B2

(12) United States Patent
Lowe et al.

(10) Patent No.: US 10,765,660 B2
(45) Date of Patent: Sep. 8, 2020

(54) AGENT CONTAINING FLAVONOID DERIVATIVES FOR TREATING CANCER AND INFLAMMATION

(71) Applicants: Henry Lowe, West Indies (JM); Ngeh J. Toyang, Columbia, MD (US); Joseph Bryant, Baltimore, MD (US)

(72) Inventors: Henry Lowe, West Indies (JM); Ngeh J. Toyang, Columbia, MD (US); Joseph Bryant, Baltimore, MD (US)

( * ) Notice: Subject to any disclaimer, the term of this patent is extended or adjusted under 35 U.S.C. 154(b) by 0 days.

(21) Appl. No.: 15/634,115

(22) Filed: Jun. 27, 2017

(65) Prior Publication Data

US 2017/0360744 A1 Dec. 21, 2017

Related U.S. Application Data

(62) Division of application No. 14/835,198, filed on Aug. 25, 2015, now Pat. No. 9,687,469.

(60) Provisional application No. 62/084,618, filed on Nov. 26, 2014.

(51) Int. Cl.
  *A61K 31/353* (2006.01)
  *C07D 311/32* (2006.01)
  *C07D 311/60* (2006.01)

(52) U.S. Cl.
  CPC .......... *A61K 31/353* (2013.01); *C07D 311/32* (2013.01); *C07D 311/60* (2013.01)

(58) Field of Classification Search
  CPC .......................... A61K 31/353; C07D 311/32
  USPC ....................................................... 514/456
  See application file for complete search history.

(56) References Cited

U.S. PATENT DOCUMENTS 9,687,469 B2 * 6/2017 Lowe .................. A61K 31/353

OTHER PUBLICATIONS

Batra and Sharma, "Anti-cancer potential of flavonoids: recent trends and future perspectives," Biotech (2013), vol. 3, pp. 439-459. (Year: 2013).*

(Continued)

*Primary Examiner* — Craig D Ricci
*Assistant Examiner* — Janet L. Coppins
(74) *Attorney, Agent, or Firm* — Royal W. Craig; Gordon Feinblatt LLC (57) ABSTRACT

A pharmaceutical composition for the prevention and treatment of cancer with specific flavanoid-based compounds selected from among the groups of Flavone, Flavanone and Flavanol, a method for the prevention and treatment of cancer and inflammation using the specific flavonoid-based pharmaceutical compositions, a method for isolating the flavonoid-based pharmaceutical compositions from raw plant material, and a method for synthesizing said specific flavonoid-based pharmaceutical compositions.

7 Claims, 11 Drawing Sheets

| Cell Line | $IC_{50}$ (µM) | | | | | | | | | |
|---|---|---|---|---|---|---|---|---|---|---|
| | HLBT-001 | HLBT-001A | HLBT-001B | HLBT-001C | HLBT-001D | HLBT-001E | HLBT-001F | HLBT-001G | HLBT-001H | HLBT-001I |
| A498 (Kidney) | 6.1 | 6.5 | 1.2 | 38 | >50 | >50 | - | - | - | - |
| A549 (Lung) | 0.70 | 1.1 | 1.3 | 31 | >50 | >50 | - | 0.9 | 61.57 | 0.11 |
| CFPAC-1 (Pancreatic) | 0.04 | 0.68 | 0.10 | 27 | >50 | 35 | - | - | - | - |
| COLO-205 (Colon) | 25 | 13 | 16 | 34 | >50 | >50 | - | - | - | - |
| DLD-1 (Colon) | 0.11 | 1.5 | 0.18 | 32 | >50 | 45 | - | - | - | - |
| IGROV-1 (Ovarian) | 2.8 | 1.6 | 1.7 | 42 | >50 | 37 | - | - | - | - |
| MCF-7 (Breast) | 2.3 | 1.7 | 4.1 | 35 | >50 | >50 | - | - | - | - |
| MiaPaca-2 (Pancreatic) | 0.14 | 1.6 | 0.22 | 25 | >50 | 36 | - | 0.3 | - | - |
| NCI-H69 (Small lung) | 0.06 | 1.0 | 0.16 | 37 | >50 | >50 | - | - | - | - |
| PC-3 (Prostate) | >5.0 | 16 | 5.5 | 38 | >50 | >50 | - | 4.8 | - | - |
| RL (Lymphoma) | 0.03 | 0.2 | 0.03 | 16 | >50 | 16 | - | - | - | - |
| UACC-62 (Melanoma) | 4.0 | 3.0 | 0.15 | >50 | >50 | 42 | - | - | - | - |
| MV4-11 (Leukemia) | 0.02 | 1.5 | 0.19 | >50 | >50 | >50 | 1.02 | - | - | - |
| LNCap (Prostate) | 0.14 | 1.24 | 0.13 | NT | NT | NT | - | - | - | - |
| U87 (Glioma) | 0.05 | - | - | - | - | - | - | - | - | - |

(56) References Cited

OTHER PUBLICATIONS

Manthey and Guthrie, J. Agric. Food. Chem. (2002), vol. 50, pp. 5837-5843. (Year: 2002).*
Daskiewicz et al, J. Med Chem (2005), vol. 48, pp. 2790-2804. (Year: 2005).*
Dong et al, Eur. J. Med. Chem (2011), vol. 46, pp. 5949-5958. (Year: 2011).*
Wang et al, J Nat. Prod (2004), vol. 67, pp. 757-761. (Year: 2004).*
Yang et al, Filoterapia (2015), vol. 103, pp. 187-191, available online Apr. 8, 2015. (Year: 2015).*
Copending U.S. Appl. No. 15/567,118, filed Oct. 17, 2017 (now U.S. Pat. No. 10,398,674). (Year: 2017).*
Li et al, Bioorganic & Med Chem (2008), vol. 16, pp. 5434-5440. (Year: 2008).*
Copending U.S. Appl. No. 15/567,118, filed Oct. 17, 2017. (Year: 2017).*

* cited by examiner

| Cell Line | HLBT-001 | HLBT-001A | HLBT-001B | HLBT-001C | HLBT-001D | HLBT-001E | HLBT-001F | HLBT-001G | HLBT-001H | HLBT-001I |
|---|---|---|---|---|---|---|---|---|---|---|
| | | | | | IC$_{50}$ (μM) | | | | | |
| A498 (Kidney) | 6.1 | 6.5 | 1.2 | 38 | >50 | >50 | - | - | - | - |
| A549 (Lung) | 0.70 | 1.1 | 1.3 | 31 | >50 | >50 | - | 0.9 | 61.57 | 0.11 |
| CFPAC-1 (Pancreatic) | 0.04 | 0.68 | 0.10 | 27 | >50 | 35 | - | - | - | - |
| COLO-205 (Colon) | 25 | 13 | 16 | 34 | >50 | >50 | - | - | - | - |
| DLD-1 (Colon) | 0.11 | 1.5 | 0.18 | 32 | >50 | 45 | - | - | - | - |
| IGROV-1 (Ovarian) | 2.8 | 1.6 | 1.7 | 42 | >50 | 37 | - | - | - | - |
| MCF-7 (Breast) | 2.3 | 1.7 | 4.1 | 35 | >50 | >50 | - | - | - | - |
| MiaPaca-2 (Pancreatic) | 0.14 | 1.6 | 0.22 | 25 | >50 | 36 | - | 0.3 | - | - |
| NCI-H69 (Small lung) | 0.06 | 1.0 | 0.16 | 37 | >50 | >50 | - | - | - | - |
| PC-3 (Prostate) | >5.0 | 16 | 5.5 | 38 | >50 | >50 | - | 4.8 | - | - |
| RL (Lymphoma) | 0.03 | 0.2 | 0.03 | 16 | >50 | 16 | - | - | - | - |
| UACC-62 (Melanoma) | 4.0 | 3.0 | 0.15 | >50 | >50 | 42 | - | - | - | - |
| MV4-11 (Leukemia) | 0.02 | 1.5 | 0.19 | >50 | >50 | >50 | 1.02 | - | - | - |
| LNCap (Prostate) | 0.14 | 1.24 | 0.13 | NT | NT | NT | - | - | - | - |
| U87 (Glioma) | 0.05 | - | - | - | - | - | - | - | - | - |

| APO-ONE Caspase-3/7 Assay in PC-3 cells | | |
| --- | --- | --- |
| Compound | Compound ID | $IC_{50}$ (µM) |
| 1 | HLBT-001 | 34.80 |
| Reference | Staurosporine | 21.56 |

Fig. 7

| Kinases inhibited | 1° Assay (10µM) | Kd/$IC_{50}$ (µM) |
| --- | --- | --- |
| BRAF (V600E) | 70% | 2.9 |
| BRAF | 60% | 2.5 |
| EPHB6 | 54% | 5.9 |
| FLT3 (D835H) | 56% | 5.8 |
| FLT3 (D835V) | 93.7% | 0.75 |
| FLT3 (D835Y) | 57% | 6.0 |
| FLT3 (ITD.F691L) | 8% | >30 |
| VSP34 (PIK3C3) | 59% | 3.5 |
| | | |

| Name/ID | Viability (ATP) IC$_{50}$ | ROS/ATP ratio |
|---|---|---|
| HLBT-001 | >100 | 193.2 |
| ketoconazole | 21.24 | 5271 |
| Nefazodone | 31.74 | 1407 |
| Cimetidine | - | 128.9 |
| Ifosfamide | - | 146.4 |

FIG. 13

AGENT CONTAINING FLAVONOID DERIVATIVES FOR TREATING CANCER AND INFLAMMATION

CROSS-REFERENCE TO RELATED APPLICATION(S)

The present application is a division of U.S. patent application Ser. No. 14/835,198 filed on Aug. 25, 2015 which is incorporated herein by reference. U.S. patent application Ser. No. 14/835,198 in turn derives priority from U.S. Provisional Patent Application 62/084,618, filed 26 Nov. 2014, the entirety of which is incorporated herein by reference.

BACKGROUND OF THE INVENTION

1. Field of the Invention

The present invention relates to flavonoid derivatives and, more particularly, to a flavonoid derivative or the pharmaceutically acceptable salt thereof that may be used in a pharmaceutical composition for preventing and treating cancer and inflammation.

2. Description of the Background

Natural physiological cell death occurs primarily through apoptosis, i.e., a form of programmed cell death that plays a key role in our body's natural process of destroying infected or damaged cells. Cancer comprises a group of over 100 different forms of disease, all of which share a common characteristic: too little apoptosis. Cancer or tumor cells have a damaged genetic composition resulting in abnormal cell cycles and unrestrained cell proliferation.

The increased focus on cellular biology has led to a profusion of drugs to treat cancer. These drugs include alkylating agents, intercalating agents, antimetabolites, etc., most of which target DNA or enzymes regulating the DNA duplication and elongation process. However, the great majority of the drugs currently available for treatment of cancer are toxic and involve detrimental side-effects on healthy cells, tissues and organs. A successful anticancer drug should kill or incapacitate cancer cells without causing excessive damage to normal cells. Plants have long-supplied the active ingredients of traditional medicinal products. Consequently, plants are increasingly relied upon as sources for new commercially viable drug leads. Flavonoids in particular are one of the most preferred groups of natural chemotypes tested for biological activities. Flavonoids (or bioflavonoids) are a class of plant secondary metabolites. Flavonoids have low toxicity and are widely available in a variety of plants. Chemically, flavonoids have the general structure of a 15-carbon skeleton, including two phenyl rings (A and B) and heterocyclic ring (C). This carbon structure can be abbreviated C6-C3-C6.

Flavanone is a type of flavonoid represented by chemical formula 1:

Formula 1

Flavanone is generally glycosylated by a disaccharide at position seven to give flavanone glycosides.

Flavone is another class of flavonoids based on the backbone of 2-phenylchromen-4-one (2-phenyl-1-benzopyran-4-one) represented by chemical formula 2:

Formula 2

Flavonols are another class of flavonoids with the 3-hydroxyflavone backbone represented in chemical formula 3:

Formula 3

The diversity between different types of flavanols stems from the different positions the phenolic —OH groups.

The present inventors have isolated very bioactive flavonoid molecules selected from among the groups of Flavone, Flavanone and Flavanol, and has successfully tested their activity against several cancer cell lines including brain, breast, Kaposi sarcoma, leukemia, lung, melanoma, ovarian, pancreatic, colon and prostate cancer. The present invention provides a pharmaceutical composition for the prevention and treatment of cancer and inflammation with flavanoid-based compounds having the structure of the general formula of chemical formula 1 or a pharmaceutically acceptable salt thereof as an active ingredient. The present invention also provides a method for the prevention and treatment of cancer and inflammation using a flavonone-based pharmaceutical composition having the structure of chemical formula 4, as well as a method for isolating said pharmaceutical composition from raw plant material and for synthesizing said pharmaceutical composition.

SUMMARY OF THE INVENTION

It is, therefore, an object of the invention to provide a pharmaceutical composition for the prevention and treatment of cancer and/or inflammation with specific flavanoid-based compounds selected from among the groups of Flavone, Flavanone and Flavanol.

It is another object to provide a method for the prevention and treatment of cancer and/or inflammation using specific flavonoid-based pharmaceutical compositions.

It is another object to provide a method for isolating specific flavonoid-based pharmaceutical compositions from raw plant material that are biologically active in the prevention and treatment of cancer and/or inflammation.

It is still another object to provide a method for synthesizing said specific flavonoid-based pharmaceutical compositions.

In accordance with the foregoing objects, the present invention provides a flavonoid-based pharmaceutical composition for the prevention and treatment of cancer and/or inflammation having the structure of the general formula of chemical formula 4:

Formula 4 or a pharmaceutically acceptable salt thereof, wherein the groups R1-R10 may be any one or more substituents selected from the group consisting of a hydrogen molecule (H), a hydroxide molecule (OH), a methyl group comprising one carbon atom bonded to three hydrogen atoms (CH3), an alkoxy group, which includes methoxy, a carboxyl group (COOH), chlorine (Cl), Bromine (Br), Fluorine (F), Glutamic acid (Glu), and any salts or derivatives of the foregoing. A and B may each be either a single or double bond.

A method for the prevention and treatment of cancer and inflammation using the specific flavonoid-based pharmaceutical compositions above is also disclosed, as well as a method for isolating the specific flavonoid-based pharmaceutical compositions from raw plant material, and a method for synthesizing said flavonoid-based pharmaceutical compositions.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

Reference will now be made in detail to preferred embodiment of the present invention, examples of which are illustrated in the accompanying drawings.

The present invention is a group of flavanoid-based pharmaceutical compositions selected from among the groups of Flavone, Flavanone and Flavanol useful for the prevention and treatment of cancer and inflammation.

The flavonoid-based pharmaceutical composition for the prevention and treatment of cancer and/or inflammation having the structure of the general formula of chemical formula 4:

Formula 4 or a pharmaceutically acceptable salt thereof, wherein the groups R1-R10 may be any one or more substituents selected from the group consisting of a hydrogen molecule (H), a hydroxide molecule (OH), a methyl group comprising one carbon atom bonded to three hydrogen atoms (CH3), an alkoxy group, which includes methoxy, a carboxyl group (COOH), chlorine (Cl), Bromine (Br), Fluorine (F), Glutamic acid (Glu), and any salts or derivatives of the foregoing. A and B may each be either a single or double bond.

A method for the prevention and treatment of cancer and inflammation using the specific flavonoid-based pharmaceutical compositions above is also disclosed. Administration may be by various mutes including oral, rectal or intravenous, epidural muscle, subcutaneous, intrauterine, or via blood vessels in the brain (intracerebroventricular) injections. The flavonoid derivatives of the general formula of chemical formula 4 according to the present invention and a pharmaceutically acceptable salt thereof may be administered in an effective dose, depending on the patient's condition and body weight, extent of disease, drug form, route of administration, and duration, but most preferably are administered in a dose within a range of from 0.1 to 500 mg between 1-6 times a day. Of course, most dosages will be by a carrier. The specific dose level and carrier for patients can be changed according to the patient's weight, age, gender, health status, diet, time of administration, method of administration, rate of excretion, and the severity of disease.

The composition may be formulated for external topical application, oral dosage such as powders, granules, tablets, capsules, suspensions, emulsions, syrups, aerosols, suppositories, or in the form of a sterile injectable solution. Acceptable carriers and excipients may comprise lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

Isolation of Flavonoid Derivatives and Synthesis of Analogs

Figure 1:
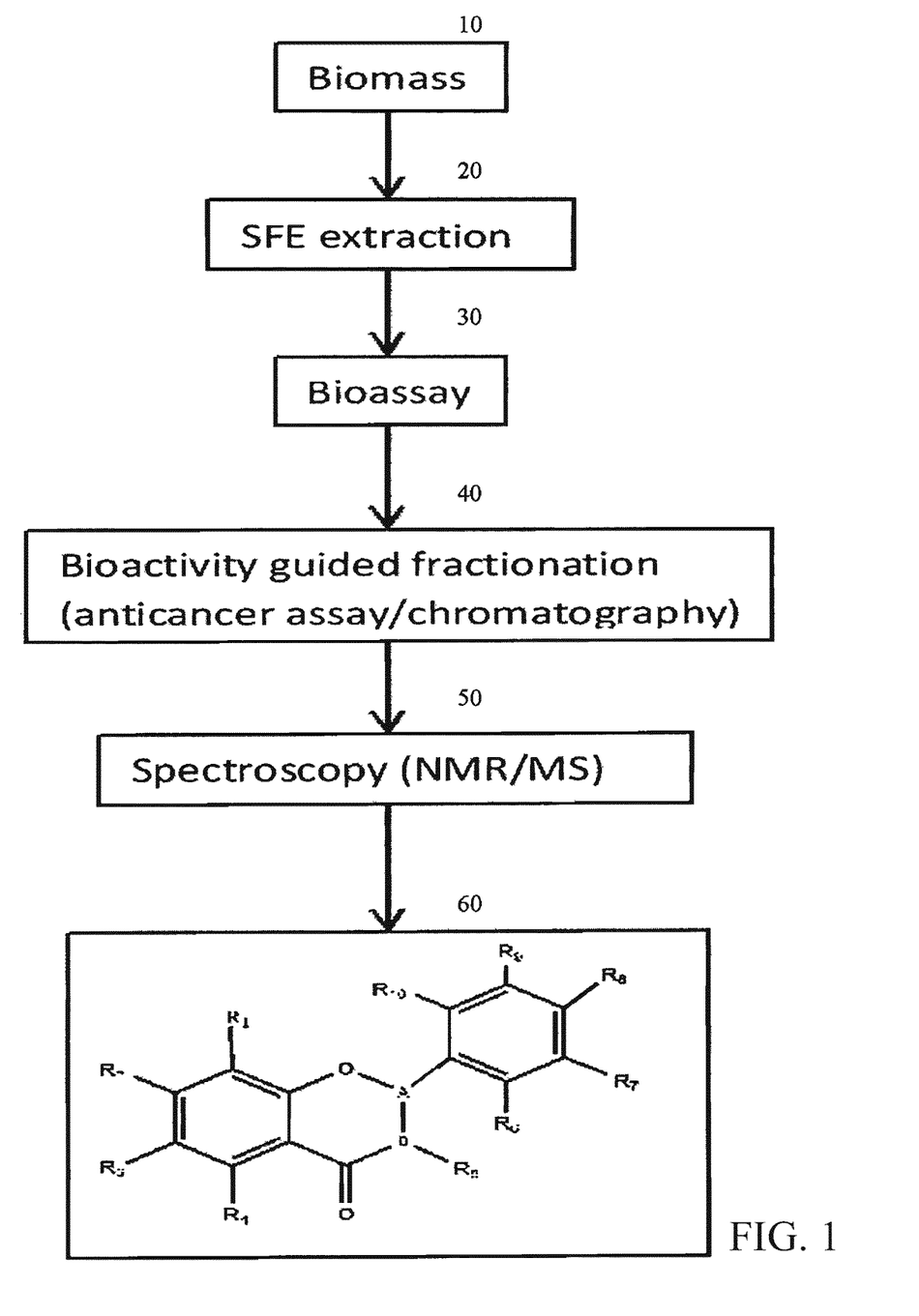
FIG. 1 is a flow diagram illustrating a suitable method for isolating the specific flavonoid-based pharmaceutical compositions from raw plant material.

A method for isolating the specific flavonoid-based pharmaceutical compositions from raw plant material is now described with reference to FIG. 1.

As shown therein, at step 10 an appropriate amount of plant biomass is collected. For present purposes, *Tillandsia Recurvata* plants were collected by hand. See, De Queiroga, M., Andrade, L., Florencio, K., et al. (2004), "Chemical constituents from *Tillandsia* recurvate", Fi-282 H. I. doi: 10.1016/j.fitote.2004.01.003 The collected plant material was air dried under shade and pulverized into powder.

At step 20 the powder is subjected to supercritical fluid extraction (SFE) by which carbon dioxide ($CO^2$) is used for separating one component (the extractant) from another (the matrix). The extract is evaporated to dryness resulting in a green residue.

At step 30, for experimental purposes, a bioassay-guided fractionation was employed, using a standard protocol to isolate a pure chemical agent from its natural origin. This entailed a step-by-step separation of extracted components based on differences in their physicochemical properties, and assessing all their biological activity. The extracted components may, for example, be fractionated by dry column flash chromatography on Si gel using hexane/CH2Cl2/ethyl acetate and mixtures of increasing polarity to yield different fractions. The sample is then degassed by ultra-sonication to yield an insoluble solid, which solid is then filtered. The sample may then be subjected to high performance liquid chromatography (HPLC) using a column Phenomenex Luna™ C18, 5 µm, 2×50 mm; eluent, acetonitrile with 0.05% MeOH to confirm the presence of the various fractions.

At step 40, bioactivity of the extracts were verified by an anticancer cell proliferation assay as described above. This identified the bioactive flavonoids from all the supercritical fluid extracts (SFE). As reported previously, the identified flavonoid-based extracts showed activity against several cancer cell lines including brain, breast, Kaposi sarcoma, leukemia, lung, melanoma, ovarian, pancreatic, colon and prostate cancer, and against inflammation.

The next step was to identify the flavonoid-based constituents responsible for the observed anti-cancer and anti-inflammatory activities and to further isolate them.

At step 50 Nuclear Magnetic Resonance Spectroscopy and mass spectrometry (NMR/MS) was performed and the interpreted spectra were consistent with flavanoid-based compositions including Flavone, Flavanone and Flavanol as identified above, and as shown in step 60. The bioactive flavonoid-based extracts found bioactive for the prevention and treatment of cancer had the structure of the general formula of chemical formula 4.

Given the known structure of the general formula of chemical formula 4, a method for synthesizing the same becomes possible. The bioactive flavonoid-based pharmaceutical composition may be synthesized by the phenylpropanoid metabolic pathway in which the amino acid phenylalanine is used to produce 4-coumaroyl-CoA.

Figure 2:
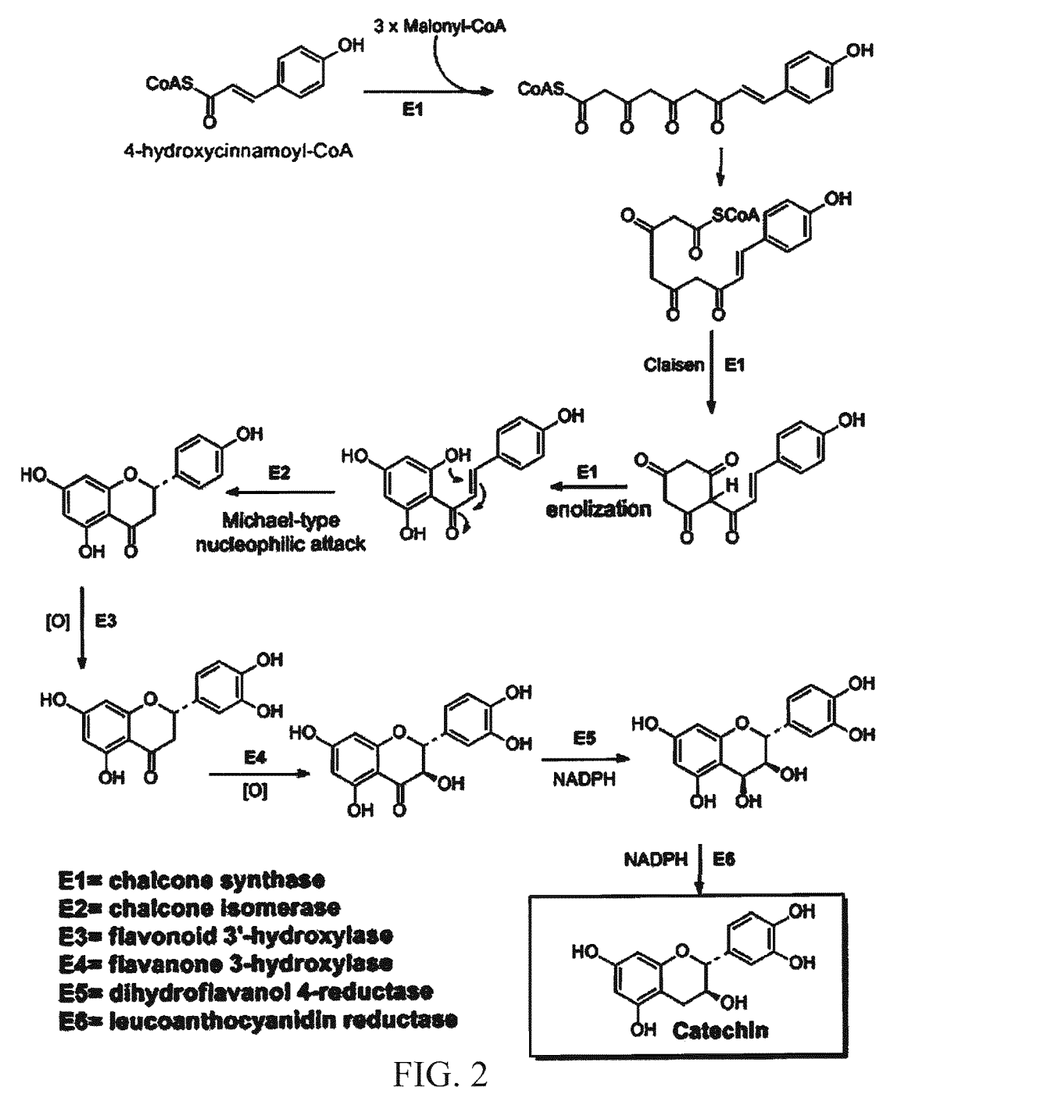
FIG. 2 is a process diagram illustrating a suitable synthesis approach according to the present invention.
Figure 3:
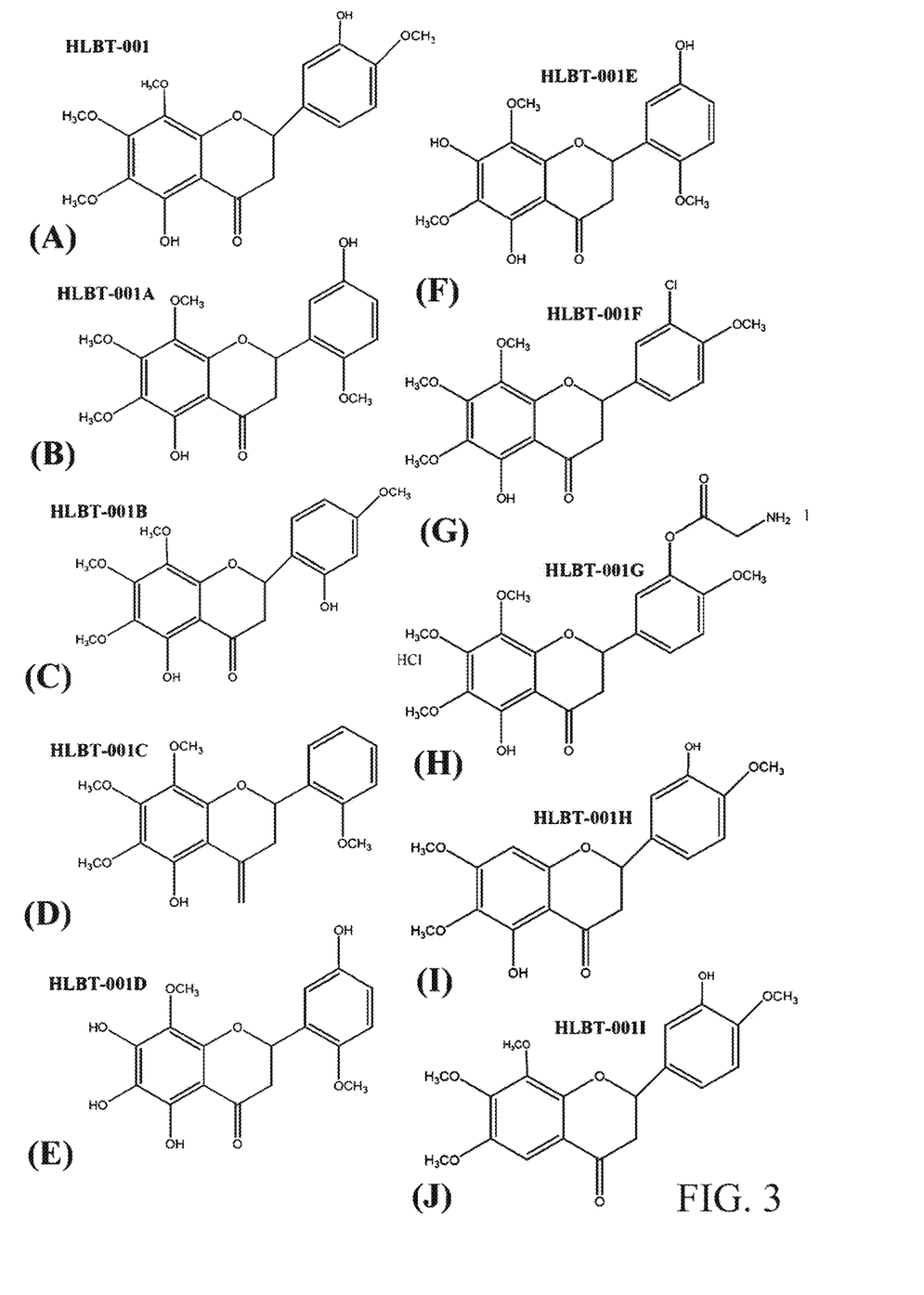
FIG. 3 is a composite (A)-(J) showing ten (10) flavonoids, including the naturally occurring molecule, which were synthesized according to the techniques of the present invention.

FIG. 2 is a process diagram illustrating a suitable synthesis approach. The 4-coumaroyl-CoA is combined with malonyl-CoA to yield the flavonoid backbone, which contains two phenyl rings. Conjugate ring-closure of chalcones results in the familiar form of flavonoids, the three-ringed structure of a flavone. The metabolic pathway continues through a series of enzymatic modifications to yield he desired Flavone, Flavanone and Flavanol as identified above, and as shown in step 60 (FIG. 1). Of course, one skilled in the art will readily understand that other methods for synthesis are possible, such as the asymmetric methods set forth in Nibbs, A E; Scheidt, K A, "Asymmetric Methods for the Synthesis of Flavanones, Chromanones, and Azaflavanones". European journal of organic chemistry (2012): 449-462. doi: 10.1002/ejoc.201101228. PMC 3412359. PMID 22876166. A total of 10 flavonoids including the naturally occurring molecule were synthesized. The synthesized flavonoids are shown in FIGS. 3(A)-3(J).

Bioactivity of Flavonoid Derivatives

Bioactivity of the above-described compound and its analogs has been verified in various anticancer assays using both CellTiter-Glo as well as the WST-1 (4-[3-(4-iodophenyl)-2-(4-nitrophenyl)-2H-5-tetrazolio]-1, 3-benzene disulfonate) colorimetric assay marketed by Roche Life Sciences®. Anticancer activity was tested against several standard cancer cell lines including brain, breast, Kaposi sarcoma, leukemia, lung, melanoma, ovarian, pancreatic, colon, renal and prostate cancers.

Upon initiation of the procedure, cells were briefly trypsinized and then plated into 96 well plates in 50 µl of media. Cells were plated at a density such that 72 hours post drug addition, the cells would be in log phase (500-2000 cells/well). The cells were then incubated overnight. Approximately 18 hours after plating, 50 µl of media containing the required flavonoid-based pharmaceutical composition was added to each well. The compounds and extracts may each be solubilized in Dimethyl sulfoxide (DMSO). The cells were then allowed to proliferate for 72 hours at 37° C. in a humidified atmosphere of 5% $CO_2$. At the end of this time period, the experiment was terminated using WST-1 cell proliferation reagent (manufactured by Roche Applied Science) in a volume of 10 µl per well. Absorbance of each sample was then read at 450 nm and 690 nm.

Figure 4:
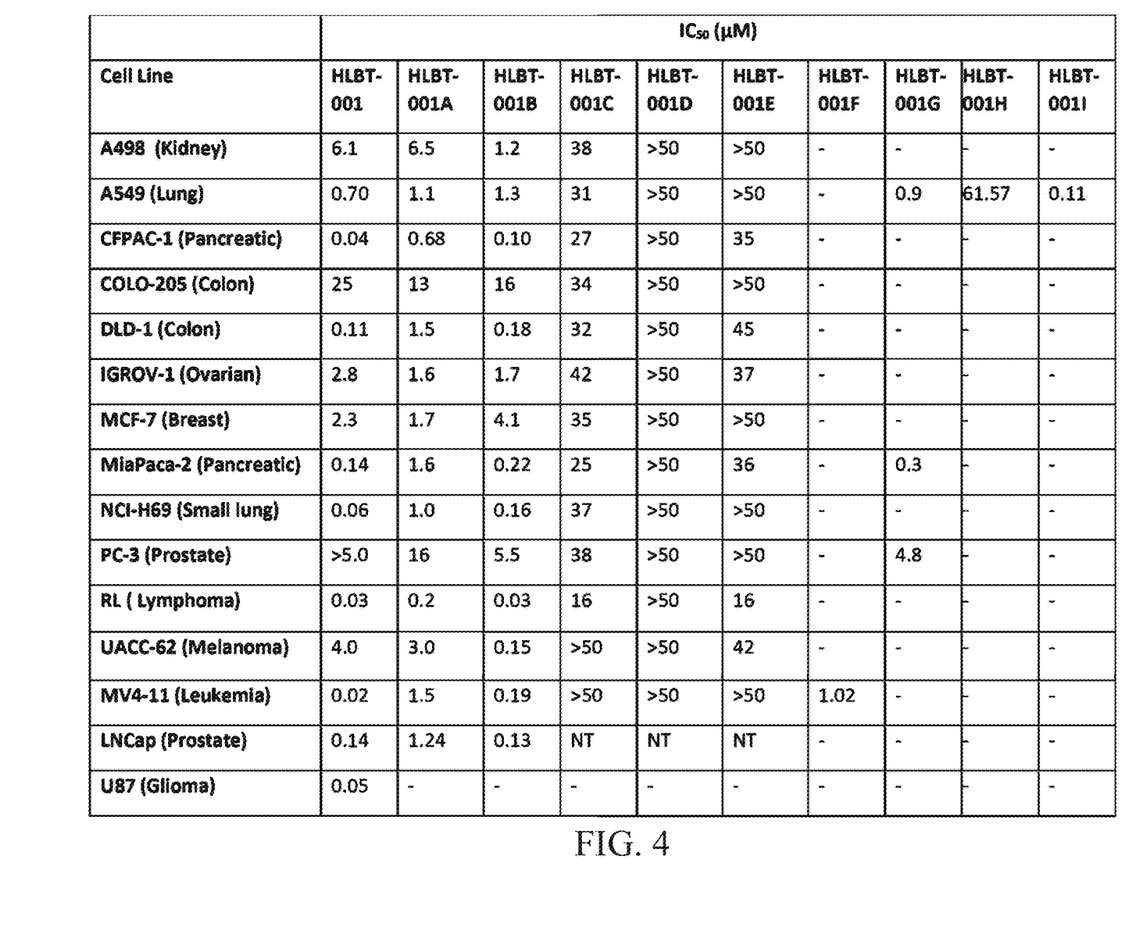
FIG. 4 is a table showing the results of the bioactivity tests on the chemical compound according to the present invention.
Figure 5:
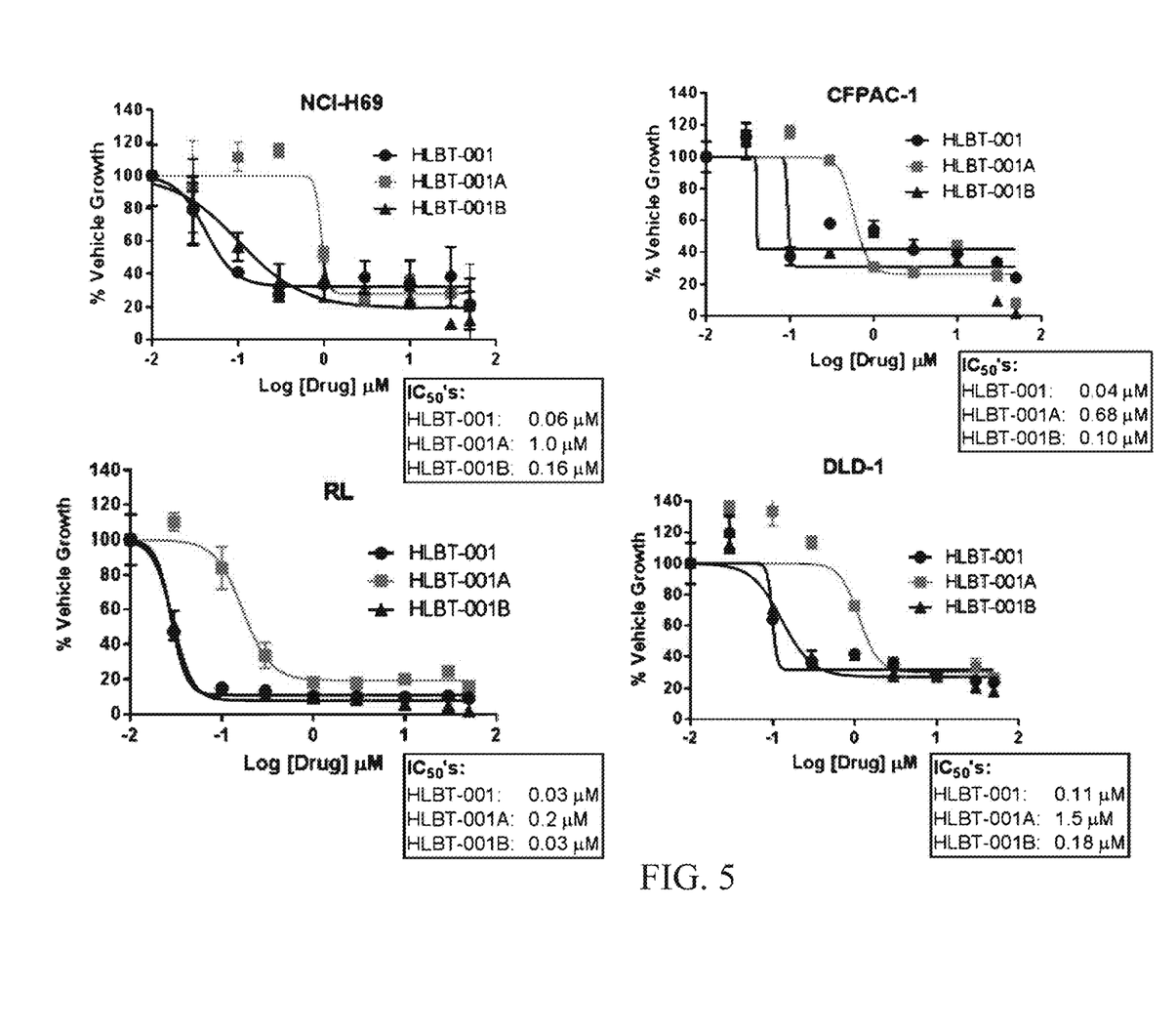
FIG. 5 is a graph showing the results of the bioactivity tests on the chemical compound according to the present invention.
Figure 6:
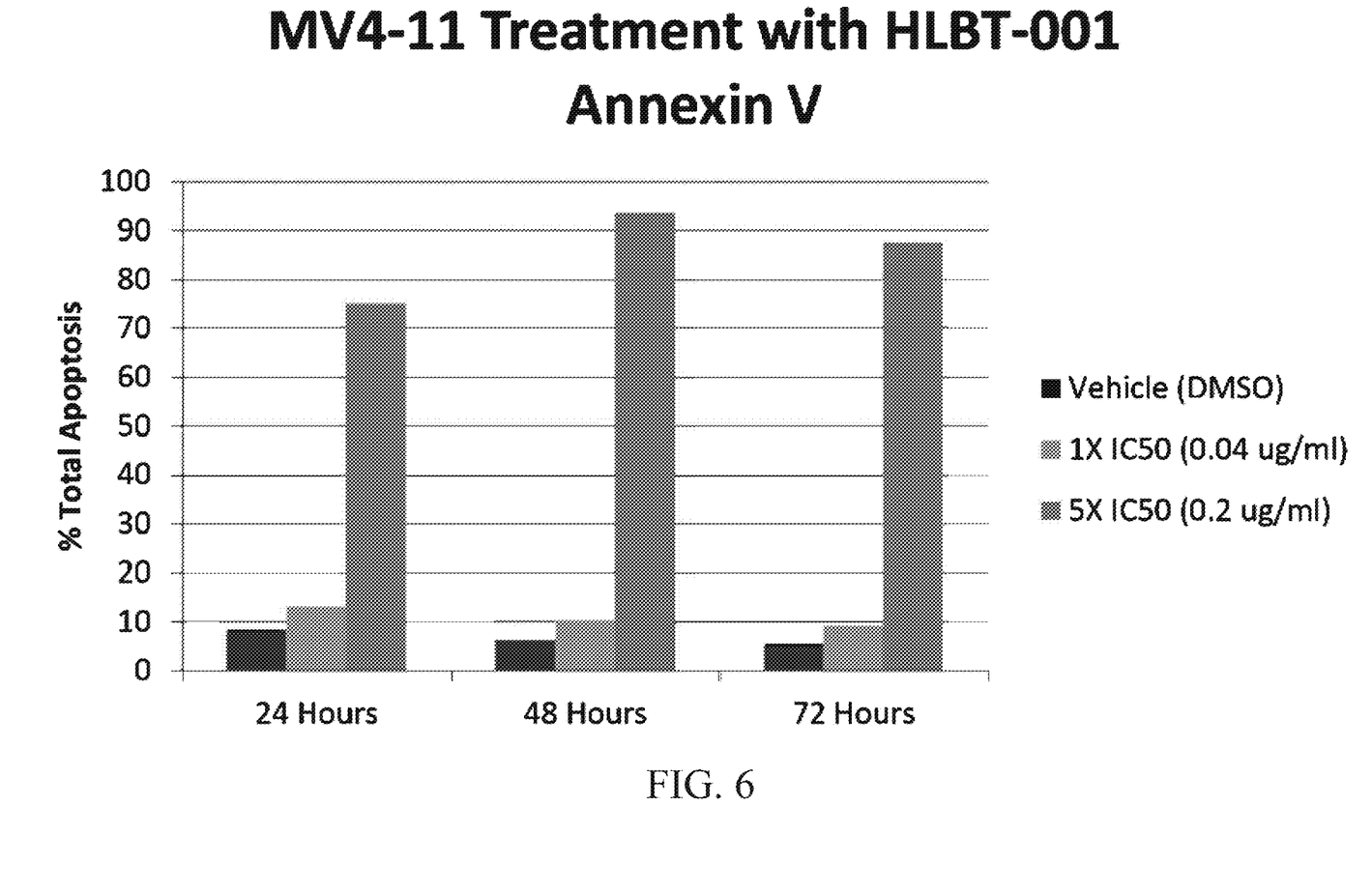
FIG. 6 is a chart depicting the results of a cell proliferation assay in which the inventive compound is shown to significantly promote apoptosis.
Figure 7:
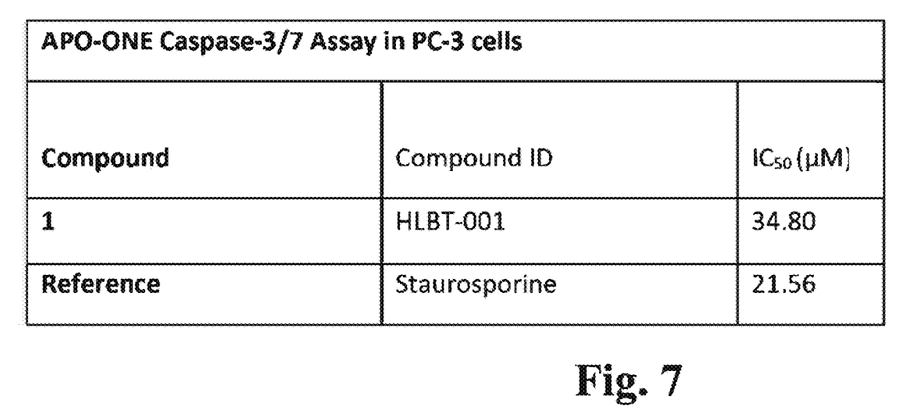
FIG. 7 is a table depicting the results of caspase 3/7 effector activity according to the present invention.

The effect of drugs on growth is assessed as percent of cell viability. The $IC_{50}$ values were determined from the extract dose versus control growth curves using Graphpad Prism® software. The procedures described above were carried out in duplicate, and the mean results as between the two sets were then determined. The results of the bioactivity are presented in FIGS. 4 and 5. After establishing the preliminary in vitro activity, the flavonoid isolate and its analogs were subjected to further studies to determine their possible mechanisms of action. The main isolate (HLBT-001) showed significant enhancement of apoptosis using the Annexin V assay run according to the assay manufacturer's instructions. At a concentration of five (5) times the $IC_{50}$ concentration in the cell proliferation assay, the compound significantly promoted apoptosis as shown in FIG. 6. To further confirm the apoptotic effect, HLBT was screened for effector activity on Caspase 3/7 using the Apo-ONE® Homogeneous Caspase-3/7 Assay kit according to manufacturer's instructions. The Apo-ONE® Homogeneous Caspase-3/7 Assay provides fast and sensitive measurement of the activities of caspase-3 and -7. Compounds in the caspase family play key effector roles in apoptosis in mammalian cells. The results of caspase 3/7 effector activity are presented in FIG. 7.

Figure 8:
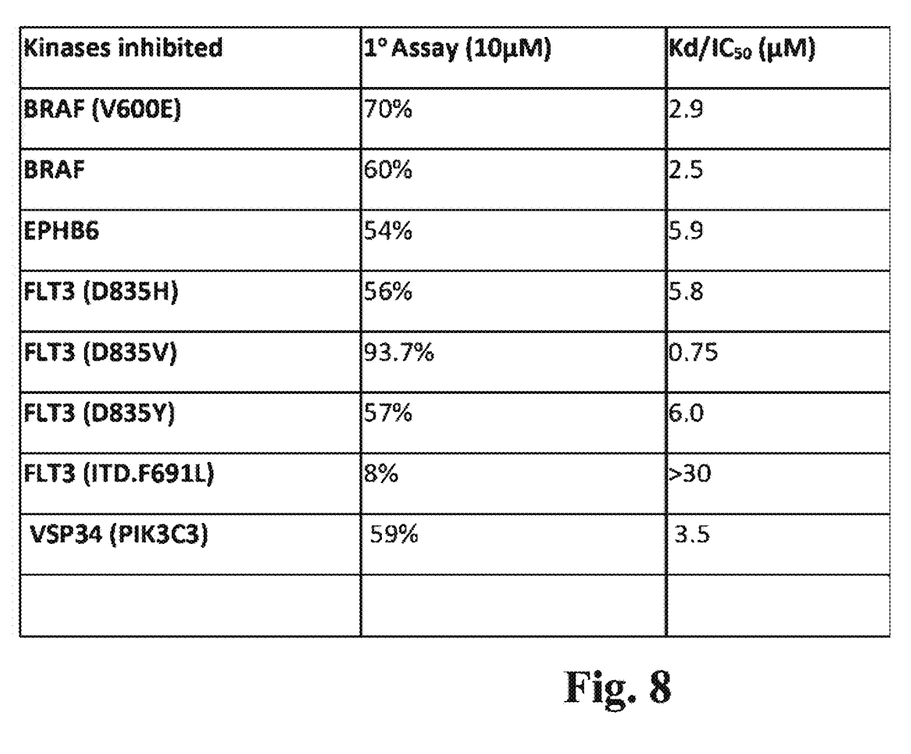
FIG. 8 is a table depicting how the flavonoid according to the present invention effectively inhibits eight (8) kinases at single digit micromolar concentrations, indicating that the anticancer activity of HLBT-001 could be via the inhibition of the overexpression of these kinases in addition to other possible factors.

To determine if the major isolate had any effect on kinases, which are enzymes that play various roles in regulating various cellular activities, and whose expression has been linked to onset and progression of several diseases including cancers, HLBT-001 was screened in a panel of over 500 protein and lipid kinases. The flavonoid effectively inhibited eight (8) kinases at single digit micromolar concentrations, indicating that the anticancer activity of HLBT-001 could be via the inhibition of the overexpression of these kinases in addition to other possible factors (See FIG. 8).

Figures 9, 10:
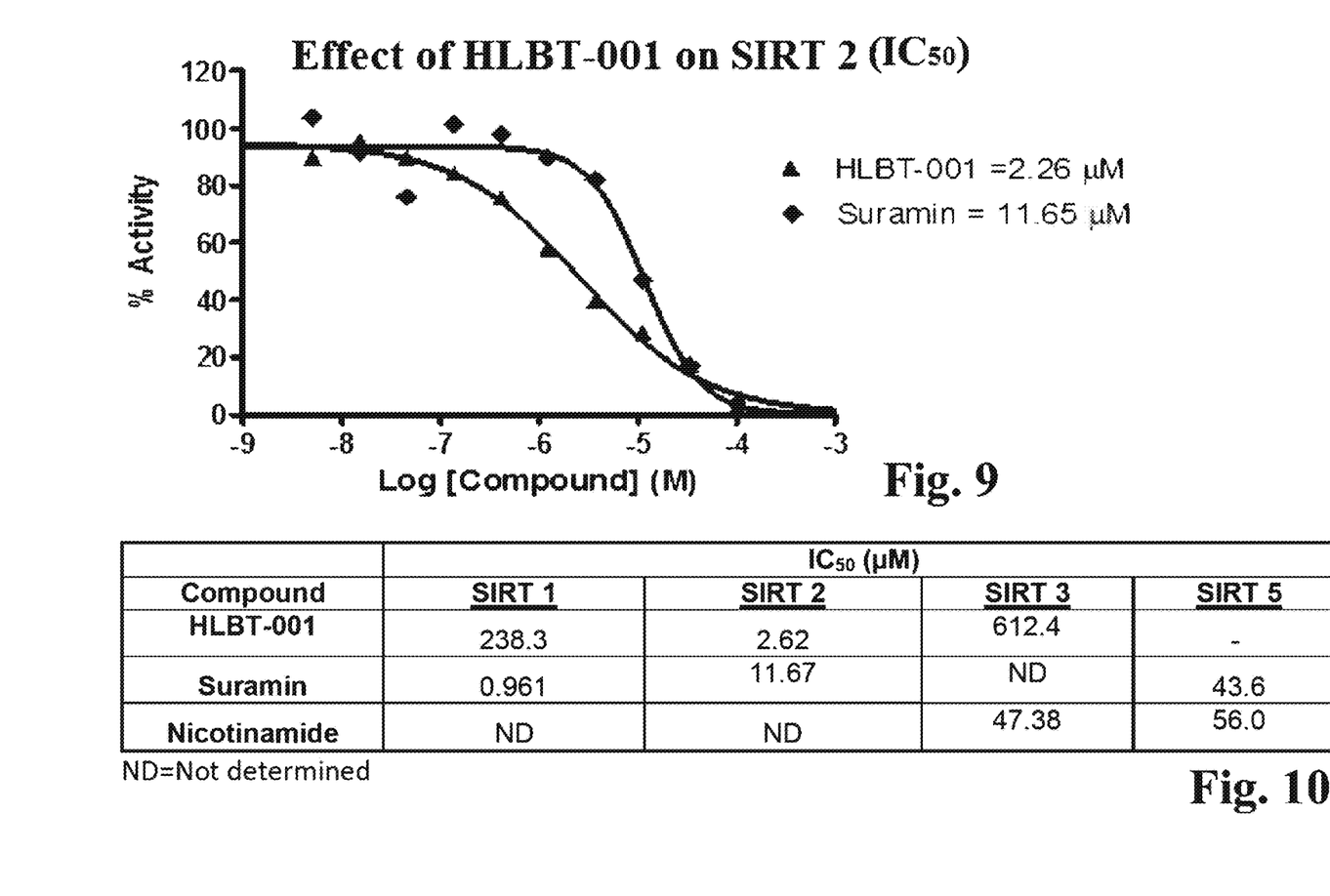
FIG. 9 is a graph showing the effect of HLBT-001 against SIRT 1, SIRT 2, SIRT 3 and SIRT 5.
FIG. 10 is a table showing the effect of HLBT-001 against SIRT 1, SIRT 2, SIRT 3 and SIRT 5.

Another mechanism that was studied involved the effect of the flavonoid compounds on sirtuins (SIRT). Several members of the SIRT family (including SIRT1-7) are a highly conserved family of NAD(+)-dependent enzymes. SIRT activity is linked to DNA repair, inflammation, neuroprotection, healthy aging, and many other processes. There is a growing interest in the discovery of small molecules altering SIRT activity because their modulation could have beneficial effects on human diseases. SIRT inhibition has been suggested in the treatment of cancer, immunodeficiency virus infections, the prevention or treatment of parasitic diseases, and neurodegenerative diseases. Studies have shown that the anti-inflammatory effects of resveratrol for example are mediated primarily by SIRT 1. For example, studies have also confirmed that the overexpression of SIRT 1 and SIRT 2 have a protumorigenic role in some cancers, making these SIRTs potential therapeutic targets (Cha, E. J., Noh, S. J., Kwon, K. S., Kim, C. Y., Park, B. H., Park, H. S., . . . & Jang, K. Y. (2009)). Expression of DBC1 and SIRT1 is associated with poor prognosis of gastric carcinoma. (*Clinical Cancer Research,* 15(13), 4453-4459). The effect of HLBT-001 was studied against SIRT 1, SIRT 2, SIRT 3 and SIRT 5. HLBT-001 showed strong activity against SIRT 2 (FIGS. 9 and 10).

Figure 11:
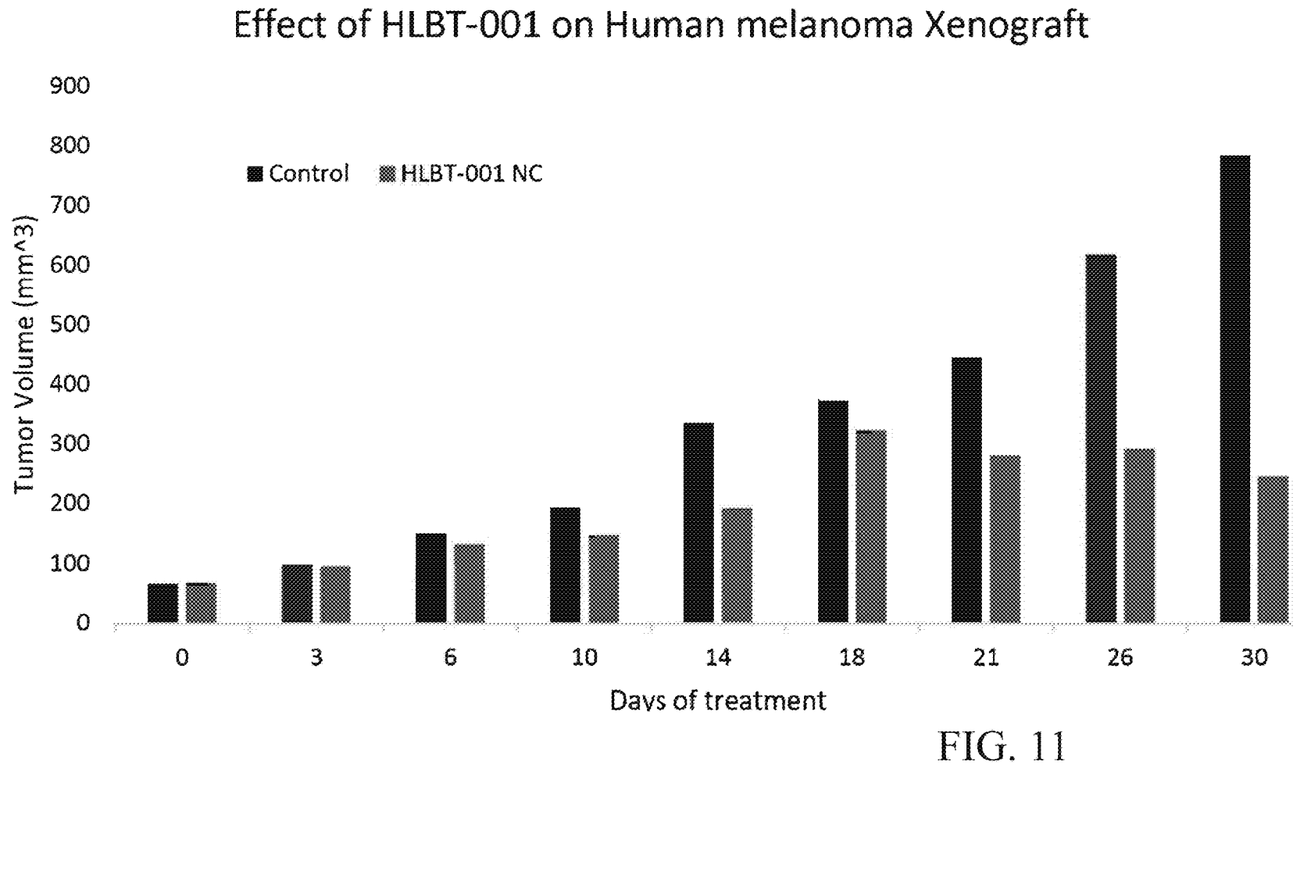
FIG. 11 is a graph showing the results of the treatment of xenograft human melanoma tumors on nude mice with HLBT-001 for a period of thirty (30) days.

To determine the preliminary activity of the HLBT-001 in vivo, xenograft human melanoma tumors on nude mice were treated with HLBT-001 for a period of thirty (30) days. The treated group had a tumor volume reduction by at least 75% compared to control (FIG. 11).

Figure 12:
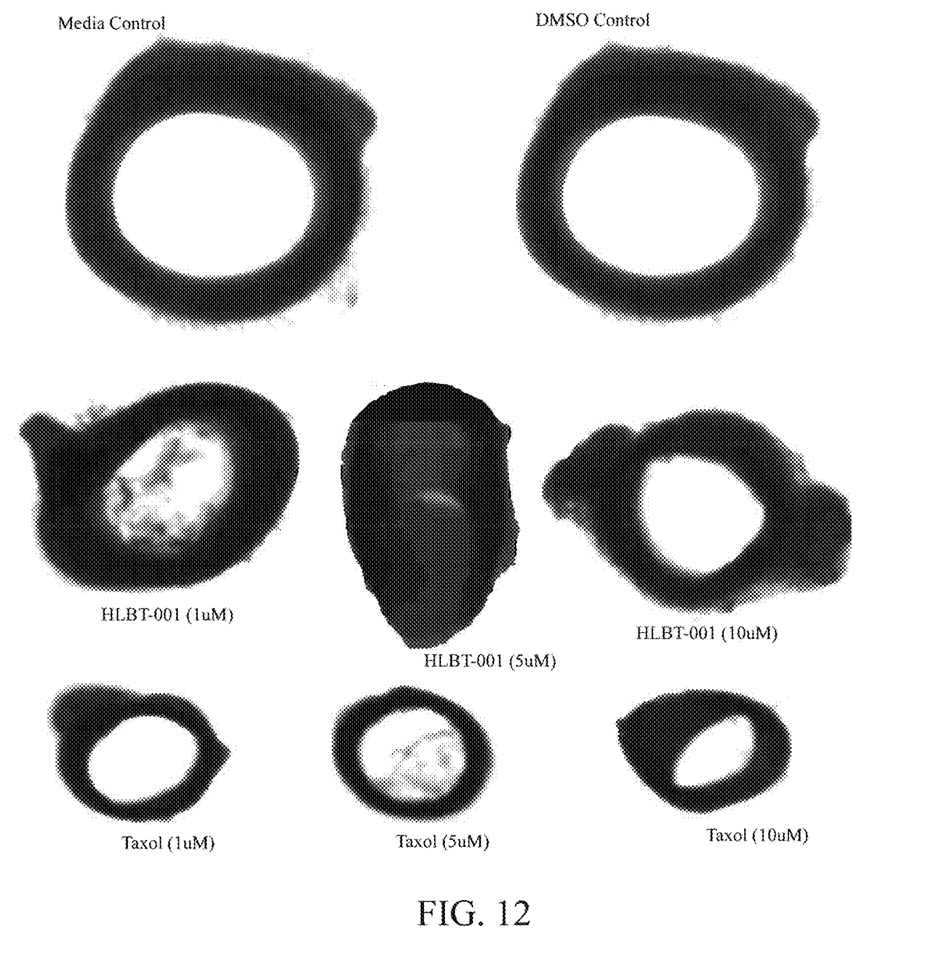
FIG. 12 is a graph demonstrating the antiangiogenic activity of HLBT-001 on rat ring aorta assay.

Evaluation of the antiangiogenic activity of HLBT was achieved in an ex-vivo rat aortic ring assay at 3 different concentrations. HLBT-001 was comparable to taxol as it inhibited sprouting of capillaries around the rat aortic ring at all 3 tested concentrations (FIG. 12). Angiogenesis is an essential step for cancer progression and dissemination. The development of new blood vessels in cancer setting (angiogenesis) is conducted by numerous physiological and pathological stimuli. The association of angiogenesis and cancer has been credited to the visionary scientist Judah Folkman (1933-2008), who was the first to state that tumor growth was directly dependent on the formation of blood vessel network development. See Folkman J, Merler E, Abernathy C, Williams G. Isolation of a tumor factor responsible for angiogenesis. *Journal of Experimental Medicine.* 1971; 133 (2):275-288. By demonstrating the potential to inhibit angiogenesis and based on previous findings presented above, HLBT-001 as such has numerous mechanisms by which it can attack cancer from growing and spreading in the human system.

Figure 13:
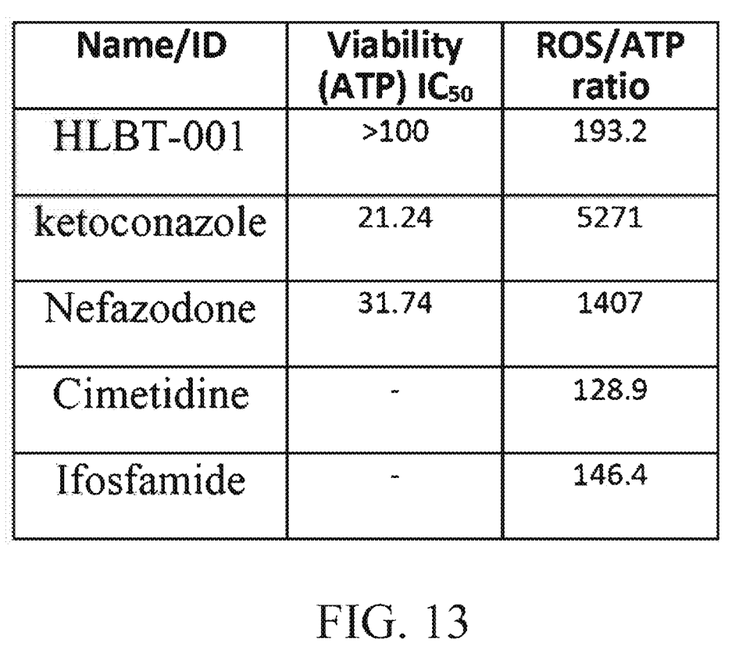
FIG. 13 table depicting how HLBT-001 shows a low ROS/ATP ratio compared to ketoconazole and nefazodone.

Determination of the potential adverse drug effect of HLBT-001 was carried out using human hepatocytes to ascertain the potential of HLBT-001 to cause severe drug induced liver injury (sDILI). Recent testing of primary human hepatocytes with a USFDA collection of 152 compounds, with known DILI potential, has led to an important discovery that the area under the log concentration-response curve (AUC) of the ROS/ATP ratio was an effective endpoint for the identification of drug associated with sDILI. HLBT-001 showed a low ROS/ATP ratio compared to ketoconazole and nefazodone, both of which are known to cause severe DILI (FIG. 13).

It should now be apparent that the above-described invention provides a pharmaceutical composition for the prevention and treatment of cancer and inflammation with specific flavanoid-based compounds selected from among the groups of Flavone, Flavanone and Flavanol, a method for the prevention and treatment of cancer using the specific flavanoid-based to pharmaceutical compositions, a method for isolating the flavanoid-based pharmaceutical compositions from raw plant material, and a method for synthesizing said specific flavanoid-based pharmaceutical compositions.

It is to be understood, therefore, that the invention may be practiced otherwise than as specifically set forth in the appended claims.

We claim:

1. A method of treating a cancer selected from a group consisting of: breast cancer, brain cancer, Kaposi sarcoma, leukemia, lung cancer, melanoma, ovarian cancer, colon cancer, renal cancer, pancreatic cancer, and prostate cancer, the method comprising the steps of:
   administering a pharmaceutical composition comprising a compound having the general chemical structure of chemical formula 4:

Formula 4 or any pharmaceutically acceptable salt thereof;
   wherein the group R1 is an alkoxy group the groups R2 and R3 are each a methoxy group or a hydroxy group, the group R6 is an alkoxy group, a hydroxyl group or hydrogen, the group R8 is an alkoxy group or hydrogen, the group R9 is a hydroxyl group, bromine, chlorine, flourine, hydroxamic acid group, amine, amide, or hydrogen; and
   wherein A-B is a single bond representing a flavanone flavonoid.

2. The method of claim 1, wherein said compound is administered in a concentration within a range of from 0.1 to 500 mg between 1-6 times per day.

3. The method of claim 1, wherein said compound is administered using a method selected from the group consisting of: rectal administration, intravenous administration via the epidural muscle, subcutaneous administration, intrauterine administration, via intracerebroventricular injections, and topically.

4. The method of claim 1, wherein said compound is administered orally.

5. The method of claim 1, wherein said compound is administered in a form selected from the group consisting of: powders, granules, tablets, capsules, suspensions, emulsions, syrups, aerosols, and suppositories.

6. The method of claim 1, wherein said compound is administered in a formulation comprising a carrier, said carrier being selected from the group consisting of: lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpynolidone, water, methyl benzoate, propyl benzoate, talc, magnesium stearate, and mineral oil.

7. A pharmaceutical composition for treating a cancer selected from a group consisting of: breast cancer, brain cancer, Kaposi sarcoma, leukemia, lung cancer, melanoma, ovarian cancer, colon cancer, renal cancer, pancreatic cancer, and prostate cancer, said pharmaceutical composition comprising a compound having the general chemical structure of chemical formula 4:

Formula 4 or any pharmaceutically acceptable salt thereof;

wherein the group R1 is an alkoxy group, the groups R2 and R3 are each a methoxy group or a hydroxy group, the group R6 is an alkoxy group, a hydroxyl group or hydrogen, the group R8 is an alkoxy group or hydrogen, the group R9 is a hydroxyl group, bromine, chlorine, fluorine, hydroxamic acid group, amine, amide, or hydrogen; and wherein A-B is a single bond representing a flavanone flavonoid.

* * * * *